United States Patent [19]
Perodjon

[11] 4,352,294
[45] Oct. 5, 1982

[54] OPTICAL SYSTEM FOR SCANNING A PART WITH A BEAM AND ESPECIALLY AN ULTRASONIC OR ELECTROMAGNETIC BEAM

[75] Inventor: Jean Perodjon, Saint Ismier, France

[73] Assignee: Commissariat a l'Energie Atomique, Paris, France

[21] Appl. No.: 185,517

[22] Filed: Sep. 9, 1980

Related U.S. Application Data

[63] Continuation of Ser. No. 30,866, Apr. 17, 1979, abandoned.

[30] Foreign Application Priority Data

Apr. 20, 1978 [FR] France .................... 78 11670

[51] Int. Cl.³ .......................................... G01N 29/04
[52] U.S. Cl. ............................ 73/642; 350/432; 356/239
[58] Field of Search ............... 73/642; 356/239; 350/189, 193, 175 FS, 175 LD, 432, 433, 434, 447

[56] References Cited

U.S. PATENT DOCUMENTS

| | | | |
|---|---|---|---|
| 3,028,752 | 4/1962 | Bacon | 73/642 |
| 3,233,449 | 2/1966 | Harmon | 73/642 |
| 3,924,453 | 12/1975 | Clark et al. | 73/642 |
| 3,974,684 | 8/1976 | Roule | 73/642 |

*Primary Examiner*—James J. Gill
*Attorney, Agent, or Firm*—Michael N. Meller; Anthony H. Handal

[57] ABSTRACT

The constructional arrangement and position of an optical system with respect to a part under inspection are such that the caustic formed within the part by the optical system by refraction of an ultrasonic or electromagnetic beam is concentrated on an axis at right angles to the surface of the part. Scanning of parts having different shapes can be performed to any predetermined depth by means of a single focusing transducer while a constant distance is maintained between the part and the transducer.

7 Claims, 10 Drawing Figures

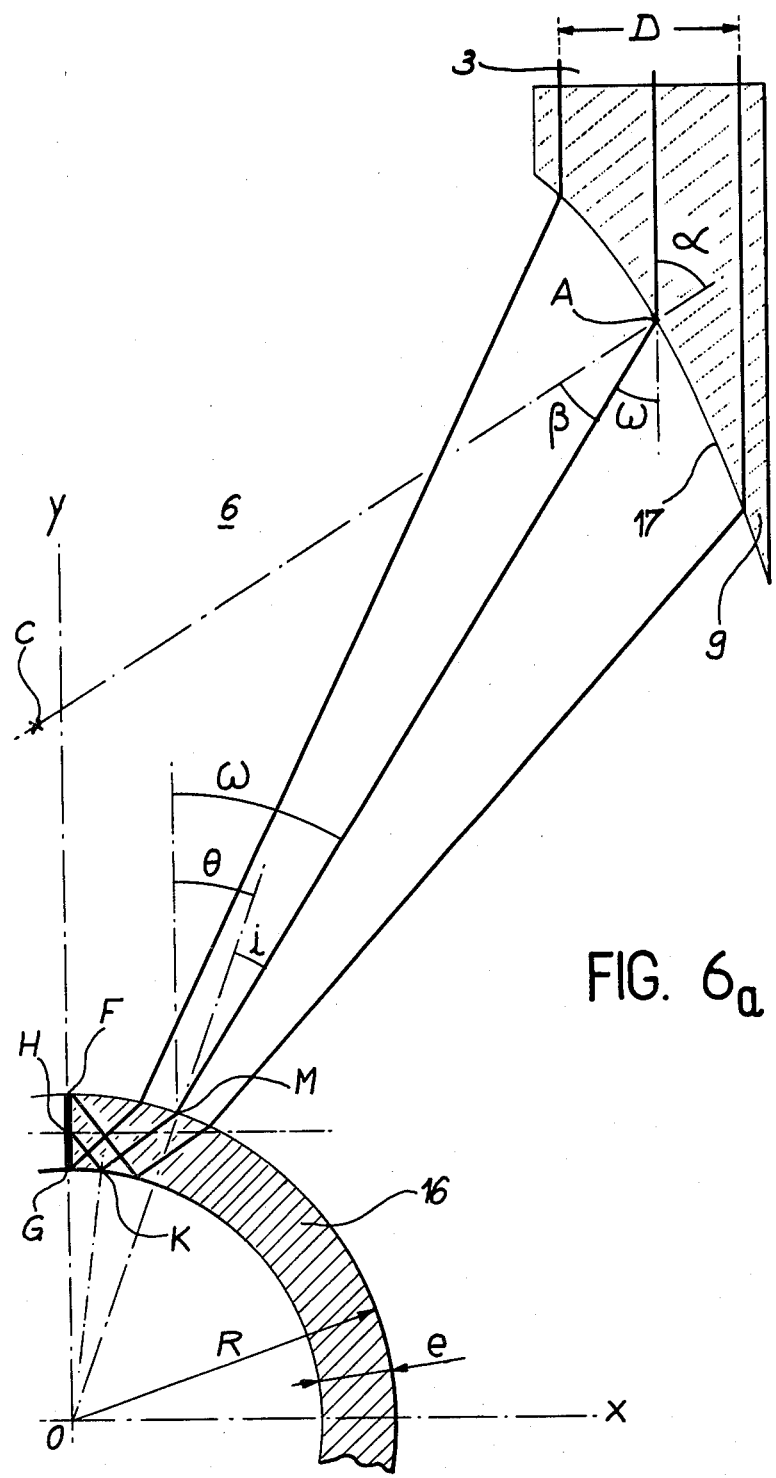

OPTICAL SYSTEM FOR SCANNING A PART WITH A BEAM AND ESPECIALLY AN ULTRASONIC OR ELECTROMAGNETIC BEAM

This is a continuation of application Ser. No. 30,866 filed Apr. 17, 1979, now abandoned.

This invention relates to an optical system for scanning a part with a beam, especially of the ultrasonic or electromagnetic type.

This invention applies more especially to deep scanning of a part in a direction at right angles to the surface of said part. Thus a given thickness of parts having different shapes can be inspected at a given instant of the scanning operation by means of a single transducer, for example, the distance between transducer and part being maintained constant. The ultrasonic transducer must accordingly be connected to a transmitter-receiver instrument of the type designated as CGR-R7 and marketed by the CGR Company, or of the type known as Kroutkramer USIP 11 and marketed by the Kroutkramer Company (France).

In order to have good sensitivity, it is necessary in known scanning devices to ensure maximum concentration of the ultrasonic waves in the vicinity of the point to be inspected. For this reason, the beams which emerge from known ultrasonic transducers are usually focused. It is known that a focused beam makes it possible to scan a segment located especially within a metallic part, for example in a zone which is in the vicinity of a welded joint formed in said part. This scanning operation is often carried out at variable depths in parts of substantial thickness or massive parts; in this case the beam must be focused on the different points to be examined. This focusing can be obtained by displacement of a single transducer. It is known that, when making use of a spherical focusing transducer, this displacement must be carried out obliquely with respect to the metal part in order to maintain the focal spot of the transducer on the segment to be scanned. Should the scanning operation consist in inspecting a welded joint between two parts by means of an ultrasonic beam, the plane of said joint is usually at right angles to the refracting surface formed by the medium containing the weld and the couplant medium (such as water, for example) in which the transducer is located. Complete observation of the weld plane is then performed by displacement of the transducer in two directions: a first displacement of the transducer in a direction parallel to the weld plane and parallel to the surface which separates the two media and a second displacement in height in order to modify the depth of the focal spot of the transducer within the part.

In order to perform deep inspection of parts, especially in a direction at right angles to the surface of said parts, it is also a known practice to employ a plurality of focusing transducers such that the focal spots within the part are located successively at different depths. This known arrangement makes it necessary to employ a large number of transducers if it is desired to obtain a sufficiently complete scan. The main disadvantage of this assembly design arises from the need to employ a large number of transducers associated with electronic equipment units, with the result that this system of assembly is very costly.

The focusing transducers which are usually employed in both types of known devices described in the foregoing often have a spherical or even toric shape.

The aim of this invention is to overcome the disadvantages of the known devices mentioned above and especially to permit deep scanning of parts without entailing the need either to displace a transducer in a number of different directions or to make use of a number of transducers.

The invention is directed to an optical system for scanning a part with a beam in which the constructional arrangement and position of the optical system with respect to the part are essentially intended to ensure that the caustic formed by said system within said part by refraction of the beam is concentrated on an axis at right angles to said part.

In this manner, the energy of the beam is no longer concentrated at one point within the part but along a segment at right angles to the part. The length of said segment can correspond in particular to the length to be inspected. Since the acoustic paths from the emitter to the caustic are equal in respect of all the points of the caustic, it is therefore merely necessary to have a narrow electronic gate in order to record the information relating to the zone being scanned at any given instant.

In accordance with a particular feature, the caustic is formed after at least one reflection of the beam within the part as a result of refraction.

In accordance with an advantageous feature, the beam which is incident upon the optical system is parallel to the caustic within the part.

In accordance with a further distinctive feature of the invention, the optical system consists of a lens.

In accordance with another distinctive feature, said optical system consists of a lens such that the lens face which receives the incident beam is flat and perpendicular to the caustic and that the lens face located opposite to the part is a skew surface having the same axis as the caustic.

In accordance with yet another distinctive feature, the optical system according to the invention is distinguished by the fact that the lens face located opposite to the part has a conical shape in the case of a flat part.

In accordance with still another distinctive feature, the optical system according to the invention is distinguished by the fact that the lens face located opposite to the part has a toric shape in the case of a spherical part.

In accordance with again another distinctive feature of the optical system according to the invention in the case of a part having a cylindrical surface, the lens face located opposite to the part has a conical surface in the vicinity of the meridian plane of said part which contains the caustic, and a toric surface in the vicinity of the equatorial plane of said part which contains the caustic, these two surfaces being joined together in a continuous and uniform manner.

The invention is also concerned with applications of the above-mentioned optical system to the scanning of massive parts.

In a particular application, said scanning operation is performed on parts having two parallel faces.

In an advantageous application of the aforementioned optical system, scanning is performed by means of an ultrasonic beam.

Finally and in another application, said optical system can be employed for medical diagnosis.

Further distinctive features and advantages of the invention will be more clearly brought out by the following description, reference being made to the accompanying drawings, wherein:

FIG. 6a illustrates a lens according to the invention for viewing a hollow spherical part having two parallel faces;

Figure 1:
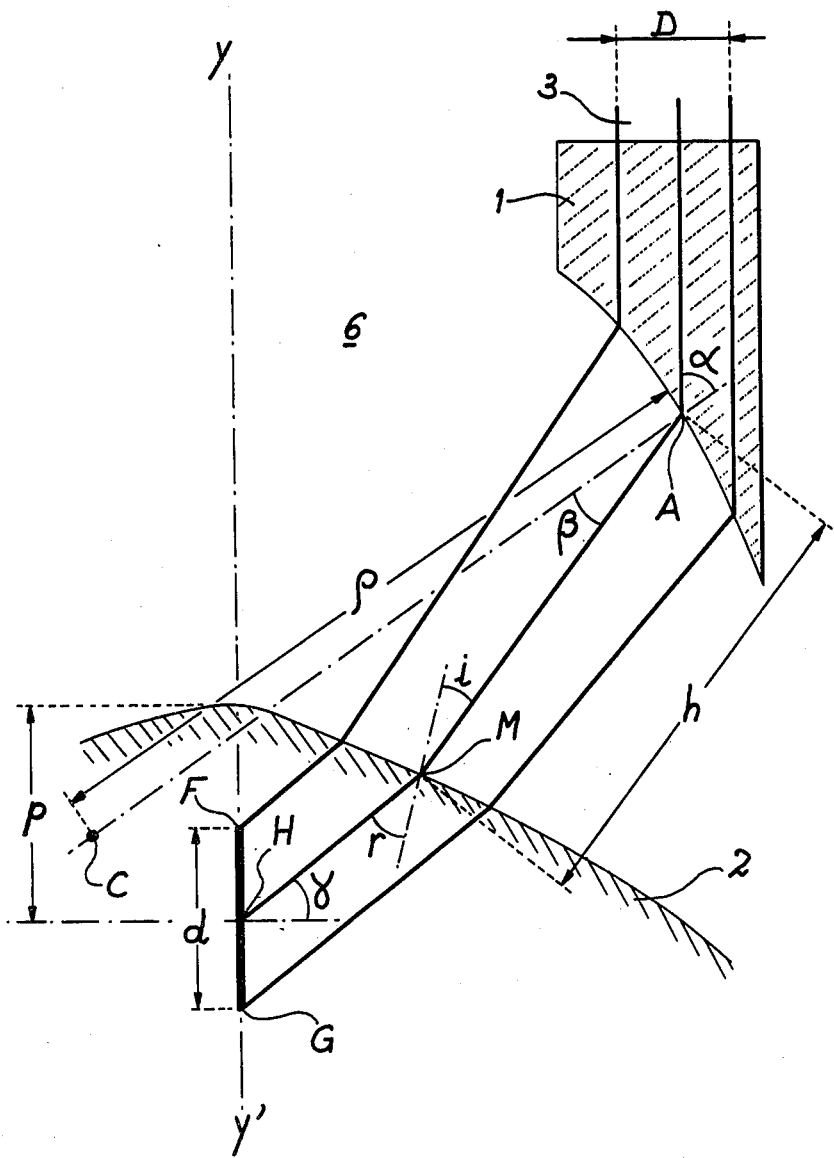
FIG. 1 is a general illustration of a lens for scanning a part with a beam. In accordance with the invention, the constructional arrangement and position of said lens with respect to the part are such that the caustic formed by said optical system within the part by refraction of the beam is concentrated on an axis at right angles to said part.

Referring now to FIG. 1, there has been shown very diagrammatically an optical system 1 for scanning a part 2 with a beam 3. In accordance with the invention, the constructional arrangement and position of said optical system are such that the caustic formed by said system within the part after refraction of the beam and represented by the segment FG is concentrated on an axis Y—Y' at right angles to said part. It will be assumed throughout the following description that the beam 3 is an ultrasonic beam, the rays of which are parallel to the axis Y—Y' and that the optical system 1 is a lens such that the lens face which receives the incident beam is flat and perpendicular to the axis Y—Y'. All that will be described below in connection with an ultrasonic beam, however, could clearly apply to a beam of the electromagnetic type. Similarly, all that will be described in relation to a lens would be equally applicable to an optical system constituted by one or a number of lenses and/or mirrors. For the sake of convenience of illustration, it has been assumed that the normals to the part along the cross-section of said part in the plane of the figure were all contained in said plane, at least in the vicinity of the mean point of incidence of the beam upon the part. Moreover, there has not been shown in the figure the ultrasonic transducer for emission of the ultrasonic wave beam 3 as well as reception of waves reflected or diffracted within the part. The following symbols and notations have been adopted in this figure:

$C_1$: the ultrasonic velocity within the lens 1;
$C_2$: the ultrasonic velocity within the couplant medium 6 between the lens 1 and the part 2. This couplant medium can consist of water, for example;
$C_3$: the ultrasonic velocity within the part 2;
$\gamma$: the angle of incidence of the beam emerging from the lens upon the caustic FG of the lens within the part;
p: the mean depth of the segment FG;
d: the length of the segment FG;
h: the mean height of the couplant medium;
A: the mean point of emergence of the beam at the exit of the lens;
a,b: the coordinates of A;
c: the center of curvature of the lens face from which the beam emerges;
u,v: the coordinates of C;
$\rho$: the radius of curvature AC;
D: the minimum width of the beam which is incident upon the lens;
H: the mean point of the segment FG;
M: the mean point of incidence of the beam upon the art;
$\alpha$: the angle of incidence of the beam at the refracting surface between lens and couplant medium;
$\beta$: the angle of refraction at the refracting surface between lens and couplant medium;
i: the angle of incidence at the refracting surface between couplant medium and part;
r: the angle of refraction at the refracting surface between couplant medium and part.

It may be stated in broad terms that the angle $\gamma$ which represents the incidence of the refracted beam on the segment FG must be constant in all the cross-sections of the part in planes containing FG, at least in the vicinity of the axis of the beam within the part, in order to ensure that the segment FG represents the caustic of the optical system within said part. Thus:

$$\gamma = \text{constant} \tag{1}$$

It is also necessary to ensure that Descartes' law is satisfied in the case of the two refracting surfaces:

$$\sin i = (C_2/C_3)\cdot\sin r \tag{2}$$

$$\sin \alpha = (C_1/C_2)\cdot\sin \beta \tag{3}$$

whence it is possible to deduce by differentiation:

$$d\gamma = 0 \tag{4}$$

and $$\cos i \cdot d\, i = (C_2/C_3) \cos r \cdot dr \tag{5}$$

Figure 2:
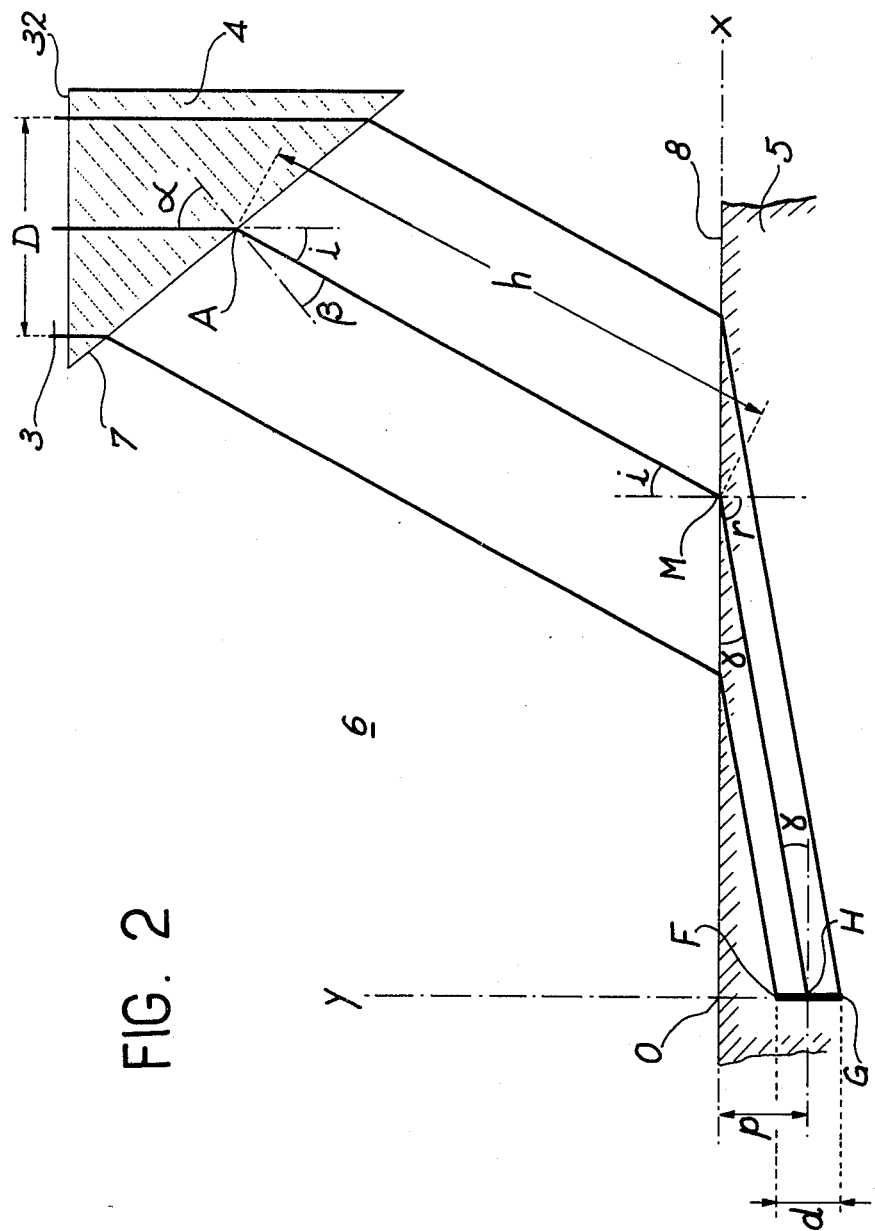
FIG. 2 illustrates a lens in accordance with the invention for scanning flat parts.

Referring now to FIG. 2, a lens 4 according to the invention is shown very diagrammatically and serves to scan a flat part 5. The constructional arrangement and position of said lens are such that the caustic of the lens within the part as represented by the segment FG is concentrated in the vicinity of a normal OY to the surface OX of the part. The ultrasonic beam 3 which is incident on the lens is parallel to the caustic within the part and the lens face 32 which receives the incident beam is flat and perpendicular to OY.

As a function of the general data and relations defined in connection with FIG. 1, we may write:

$$\alpha - \beta = i \tag{6}$$

The result of relations 3 and 6 is that:

$$tg\, \alpha = \sin i/(\cos i - C_2/C_1) \tag{7}$$

and that, on the other hand, $$r = (\pi/2) - \gamma \tag{8}$$

On the basis of relations 8 and 2, we may write:

$$\sin i = (C_2/C_3)\cdot\cos \gamma \tag{9}$$

Relations 9 and 7 make it possible to calculate the angle $\alpha$ of incidence of the beam on the refracting surface between the lens 4 and the couplant medium 6, which is constant. Since this angle $\alpha$ is constant, the section of the lens represented by the lens face 7 located opposite to the surface 8 of the part 5 in the plane of the figure is a straight-line segment which makes the angle $\alpha$ with OX. As a result of symmetry of revolution about OY, it is deduced therefrom that the surface of the lens located opposite to the part is conical.

The coordinates a, b, of the mean point A of emergence of the beam at the lens exit are accordingly as follows:

$$a = p\, tg\, r + h \sin i \quad (10)$$

$$b = h \cos i \quad (11)$$

The width D of the beam can then be expressed by the relation:

$$D = \frac{\cos \alpha \cdot \cos i \cdot tg\, r}{\cos(\alpha - i)} \cdot d \quad (12)$$

If a lens of Plexiglass is employed, for example, for scanning a flat part of steel by means of an ultrasonic beam and if the couplant medium chosen is water, the ultrasonic velocity in the lens is:
$C_1 = 2730\ m/s$
the ultrasonic velocity in water is:
$C_2 = 1483\ m/s$, and
the ultrasonic velocity $C_3$ in the part $= 3230\ m/s$ (transverse waves).

If the angle of incidence of the ultrasonic beam on the caustic FG is chosen so that $\alpha = 15°$ and if the following values are adopted:
mean scanning depth:
p = 6.9 mm
length of segment FG:
d = 4.6 mm,
mean height of water:
h = 22.3 mm,
there can be deduced from the relations given above:
r = 75°
i = 26.3°
$\alpha$ = 51.5°
a = 35.6 mm
b = 20 mm
D = 10.6 mm.

Figure 3:
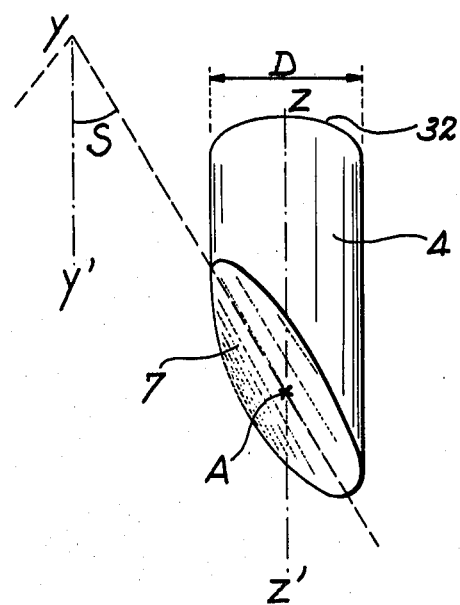
FIG. 3 shows a lens corresponding to the previous figure.

Referring now to FIG. 3, there is shown a lens 4 corresponding to the previous figure. This lens serves to scan a flat part and has a flat face 32 which receives the incident ultrasonic beam whilst the lens face 7 located opposite to the part is a skew surface which has a conical shape in the particular case of scanning of a flat part. This conical shape is obtained by intersection of a cylinder having a diameter D with a cone having an axis Y—Y' and a semivertical angle $S = \pi/2 - \alpha$. As can readily be understood, the diameter D of the cylinder which has served to prepare the lens is at least equal to the width D which was calculated previously. The axis Z—Z' of the cylinder is clearly parallel to the ultrasonic beam received by the lens on its face 32. Said axis must be located at right angles to the flat part and the point A of intersection of the axis Z—Z' with the face 7 must have coordinates a and b with respect to the part and to the axis Y—Y', a and b being given by relations 10 and 11.

Figure 4:
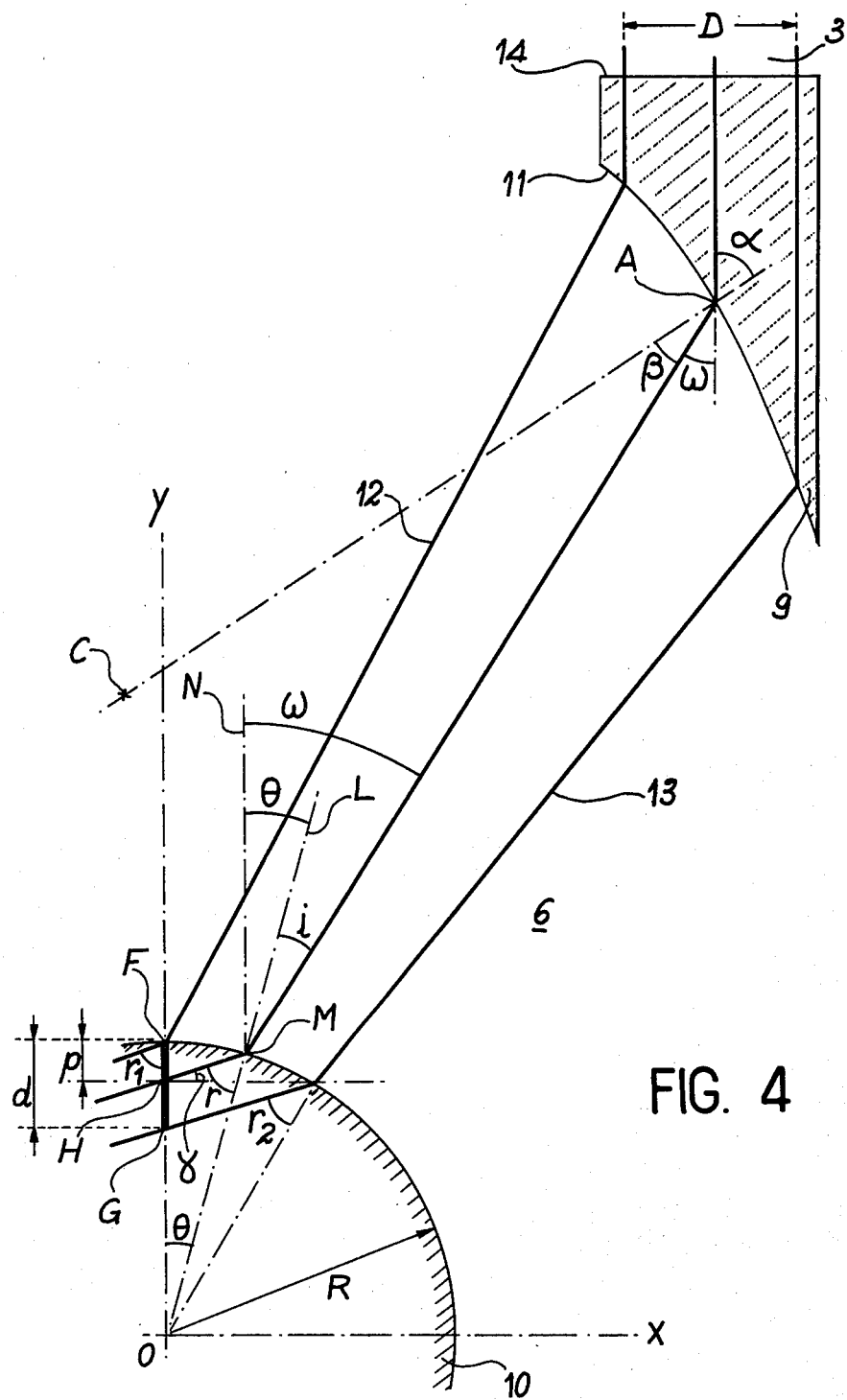
FIG. 4 illustrates a lens according to the invention for scanning spherical parts.

Referring to FIG. 4, there is shown a lens 9 for scanning a spherical part 10 with a beam 3 such as an ultrasonic beam, for example. The constructional arrangement and position of said lens with respect to the spherical part 10 are such that the caustic FG of this optical element within the part is concentrated on a normal OY to said part. The ultrasonic beam 3 which is incident on the lens is parallel to the caustic within the part and the lens face 14 which receives the incident beam is flat and perpendicular to OY. The point O represents the center of the sphere 10 of radius R. The angle $\omega$ made by the mean ray issuing from the mean point A of the lens with OY is such that:

$$\omega = \alpha - \beta.$$

If $\theta$ designates the angle made with OY by the normal to the sphere at the point M, that is to say by the radius OL of the sphere which passes through M, we also have:

$$\omega = i + \theta$$

and $$m = (\pi/2) - \gamma - \theta.$$

The radius of curvature $\rho$ of the lens face 11 located opposite to the spherical part 10 can be determined by a simple differential calculation in order to ensure that the variations in the angle of incidence $\gamma$ of the beam on the caustic FG are made stationary on each side of the mean point H. By rotation about OY, it can accordingly be deduced that the face 11 can be approached by a toric surface.

If it is considered with the notations defined earlier that the lens is cut from Plexiglass, that the couplant medium is water and that the part is of steel, we have:
$C_1 = 2730\ m/s$;
$C_2 = 1483\ m/s$;
$C_3 = 3230\ m/s$.

On the other hand, if the sphere has a radius $R = 4.8$ mm and if the angle of incidence $\gamma = 15°$, if p = 0.3 mm, d = 0.6 mm and h = 20 mm, it is possible to deduce that:
r = 64.9°;
$\theta$ = 10.1°;
i = 24.6°;
$\omega$ = 34.7°;
$\alpha$ = 63.9°;
a = 12.2 mm;
b = 21.2 mm;
$\rho$ = 15.2 mm;
and in the case of the end rays 12 and 13 of the beam, that the angles of refraction are as follows:
$r_1 = 75°$;
$r_2 = 57.7°$.

Finally, the necessary minimum width of the beam which is incident on the lens face 14 is also deduced:
D = 2.3 mm.

Figure 5:
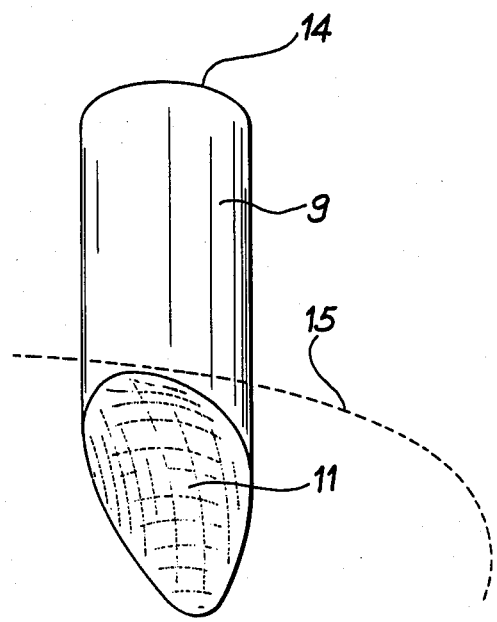
FIG. 5 shows a lens corresponding to the previous figure.

Referring to FIG. 5, there is shown a lens 9 corresponding to the optical system described above. This lens 9 has a flat entrance face 14 for the incident beam whilst the lens face 11 located opposite to the part is a surface corresponding to the intersection of a torus 15 with the cylinder from which the lens 9 is cut. The ultrasonic beam, for example, which reaches the lens is perpendicular to the face 14 and parallel to the caustic FG of the lens within the part.

The optical systems and lenses which have just been described in the case of massive parts clearly apply to non-massive parts. However in the case of parts delimited by two parallel surfaces, it can prove advantageous to obtain the caustic FG after reflection of the beam from the face of the part opposite to the face at which the beam enters the part. In the case of a plate, for example, it is only necessary to replace, in the description given in connection with the flat part shown in FIG. 2, the point H by its image in the plane mirror constituted by the face of the plate located opposite to the face at which the beam enters the part. The calculations which define the conical surface for scanning the plate are identical with those made in connection with FIG. 2. In these calculations, it is only necessary to replace the mean depth p of the segment FG by (2e−p); in this case, e designates the thickness of the plate. The result of these observations is that the numerical example given in connection with FIG. 2 corresponds to inspection of a plate having a thickness which is equal to 4.6 mm.

Referring to FIG. 6a, there is shown a lens 9 for scanning a segment FG corresponding to the caustic of the lens within the hollow sphere 16. This hollow sphere having a center O has a thickness e and an external radius R.

Figure 6B:
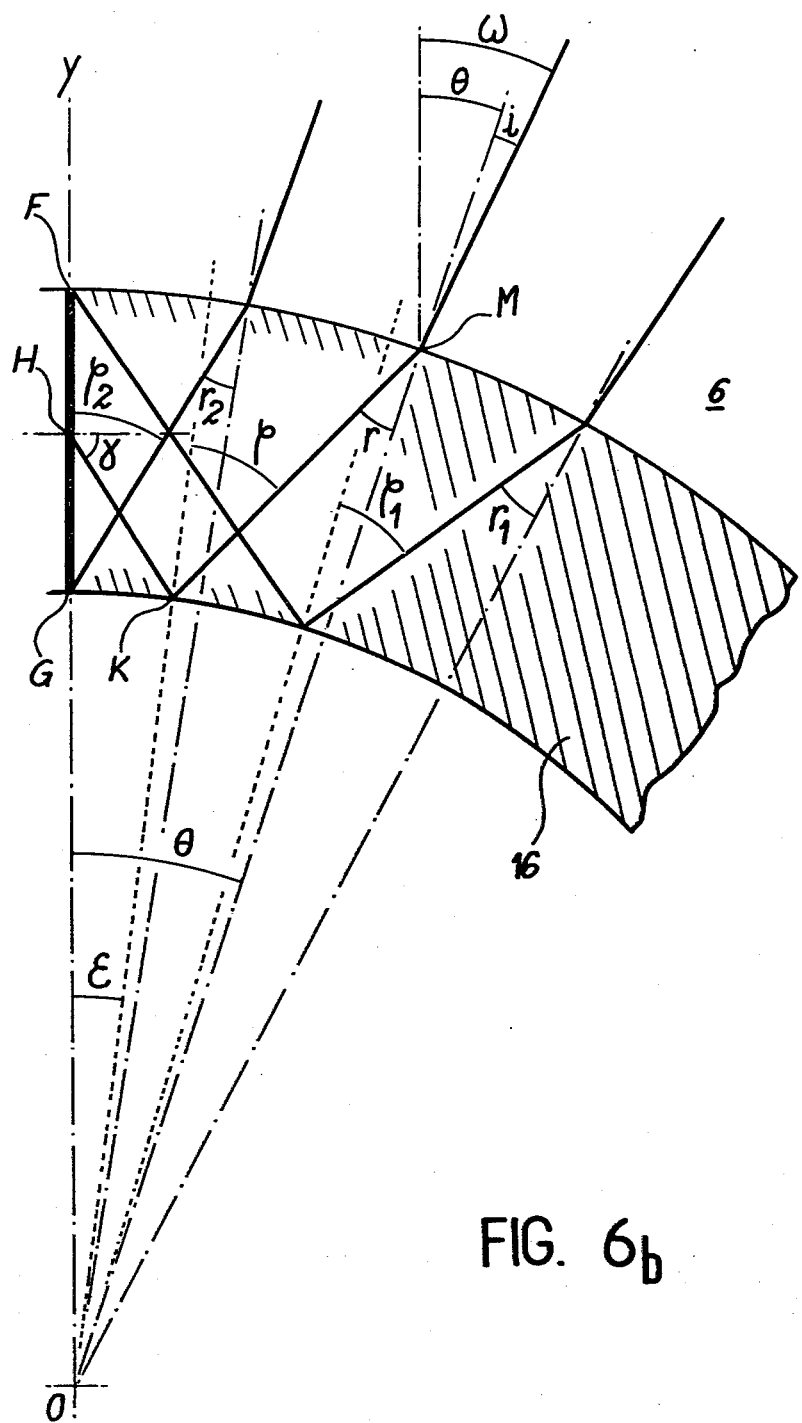
FIG. 6b is an enlarged view of the previous figure in the vicinity of the spherical part.

FIG. 6b shows an enlarged view of the portion of hollow sphere on which the beam arrives from the lens. In this figure, the following notations are adopted:

$\theta$: the angle made by the normal OY to the sphere which passes through the caustic FG with the normal to the sphere at the point of incidence M of the mean ray AM of the beam on the external face of the sphere;

$\epsilon$: the angle made by the normal OY to the sphere which passes through the caustic FG with the normal to the sphere at the point of reflection k of the mean ray MK on the internal face of the sphere;

$\phi$: the angle of incidence of the refracted beam MK on the internal face of the sphere.

The following relation can accordingly be written:

$$r + \theta - \epsilon = (\pi/2) - \gamma + \epsilon = \phi.$$

All the parameters which are necessary for determining the toric surface 17 of the lens 9 are deduced from the relation just given and by means of calculations which are similar to those made in connection with FIG. 4.

In one particular example of construction and assuming that the thickness chosen for the sphere is e=0.6 mm, that the angle $\gamma=45°$, that the radius R=4.8 mm and the mean depth p=0.3 mm are maintained, that the length of the caustic is equal to the thickness d=0.6 mm, that the mean height of water h=20 mm and that $C_1$, $C_2$, $C_3$ have the same values as in the example corresponding to FIG. 4, it is accordingly deduced that:

| | |
|---|---|
| −r = 41.5°; | −a = 10.9 mm; |
| −ϕ = 49.3°; | −b = 22.1 mm; |
| −ϵ = 4.3°; | −p = 13.7 mm; |
| −θ = 12°; | −$r_1$ = 45°; |
| −i = 17.7°; | −$r_2$ = 38.2°; |
| −ω = 29.7°; | −$\phi_1$ = 53.9°; |
| −α = 56.7°; | −$\phi_2$ = 45° |
| | −D = 3.4 mm. |

Figure 7:
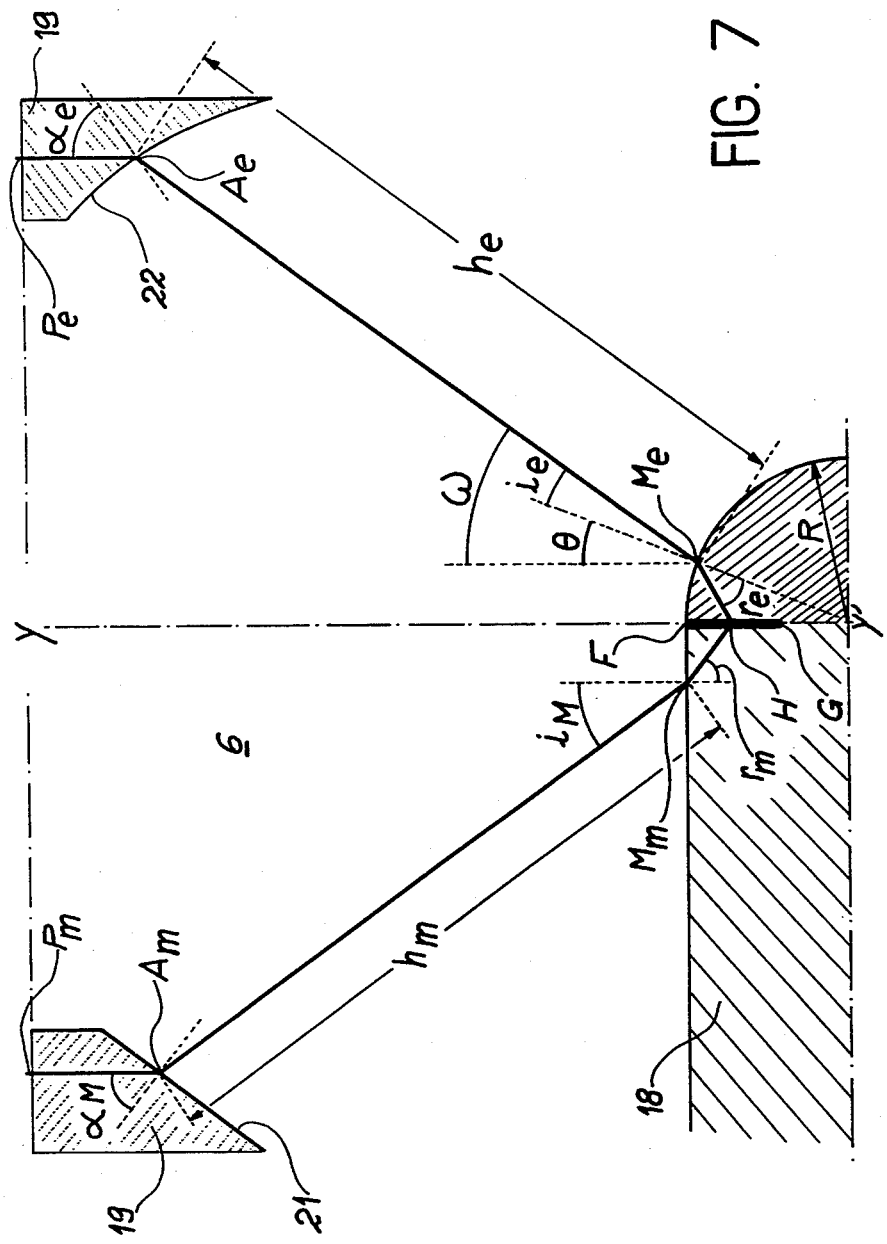
FIG. 7 illustrates a lens according to the invention for scanning a cylindrical part.

Referring to FIG. 7, there is shown a lens for scanning a cylindrical part 18 in such a manner as to ensure that the caustic FG of this optical system is located on a normal OY to the surface of said cylindrical part. It is assumed in this figure that the cylindrical part 18 is represented on the left-hand side of the normal OY along a meridian section whereas said part is represented on the right-hand side of said normal along an equatorial section. In fact, this equatorial section is represented in the figure by a displacement through an angle of 90° which brings the equatorial section of the cylindrical part in the plane of the figure. This representation has been adopted in this instance in order to facilitate the representation of the meridian and equatorial sections of the beam which emerges from the lens 19. The meridian section of the part containing the caustic FG cuts the lens 19 along a straight-line segment, the position of which is calculated as indicated in connection with FIG. 2. The lens 19 therefore has a conical surface 21 opposite to the cylindrical part 18 in the meridian section containing the caustic. The equatorial section of the part which contains FG cuts the lens 19 in a circular arc which is defined in the same manner as the arc of FIG. 4. The lens surface 22 opposite to the cylinder 18 in the equatorial section containing the caustic has a toric shape. The lens 19 must therefore have a conical surface opposite to the cylindrical part 18 in the vicinity of the meridian plane of said part which contains the caustic, and a toric surface in the vicinity of the equatorial plane of said part which contains the caustic; these two surfaces have the same axis of revolution Y—Y' and are joined together in a continuous and uniform manner; the shape of the resultant surface will be more clearly shown in FIG. 8. The heights of water he and hm are clearly related by the equality of the acoustic paths ($P_m A_m M_m H$) = ($P_e A_e M_e H$).

By way of example, if the lens is formed of Plexiglass, if the couplant medium is water and if the part to be scanned is of steel, we have:

$C_1$=2730 m/s;
$C_2$=1483 m/s;
$C_3$=3230 m/s.

Furthermore, if $\gamma=45°$ is chosen for observation without intermediate reflection of a hollow cylindrical part having a thickness e=9.5 mm, an external radius R=54.5 mm, if the observation depth p=4.75 mm or in other words if said depth corresponds to the half-thickness, and if the length d of the caustic is equal to the thickness e or in other words to 9.5 mm, if there is finally chosen for the toric portion 22 of the lens: he (height of water he in the equatorial plane)=20 mm, said height of water being the distance between the points Ae and Me in the equatorial plane, the point Ae is the point of emergence of the mean ray PeAe of the ultrasonic beam and the point Me is the point at which the mean ray reaches the cylindrical part.

In the case of the conical portion 21 of the lens, the angle of refraction $r_m$ in the meridian plane is equal to 45°, the angle of incidence in the meridian plane $i_m$=18.94° and the angle $\alpha_m$ in the meridian plane is equal to 38.88°.

The symbols $P_m$, $A_m$, $M_m$ designate the mean ray of the ultrasonic beam which passes through the lens 19 and reaches the cylinder at the point $M_m$ in the meridian plane.

By means of calculations which are comparable with those mentioned in connection with FIG. 4, the following values are obtained in the toric portion 22 of the lens:

angle of refraction $r_e$ in the equatorial plane:

$r_e = 40.20°$;
angle $\theta = 4.80°$;
angle of incidence $i_e$ in the equatorial plane:
$i_e = 17.24°$;
angle $\omega = 22.04°$;
angle $\alpha_e$ in the equatorial plane:
$\alpha_e = 44.36°$.

Under these conditions, the equality of the acoustic paths gives the mean height of water $h_m$ in the meridian plane, namely $h_m = 20.38$ mm.

The position of the mean point $A_m$ in the conical portion 21 of the lens is accordingly defined by the coordinates $a_m = 11.37$ mm and $b_m = 19.28$ mm.

Similarly, the position of the mean point $A_e$ in the case of the toric portion 22 of said lens is defined by the coordinates $a_e = 12.07$ mm, $b_e = 72.85$ mm (it should be noted that the ordinates b are displaced by $R = 54.5$ mm between the equatorial and meridian sections).

The radius of curvature $\rho$ of the toric portion of the lens is in that case equal to 61.46 mm.

Figure 8:
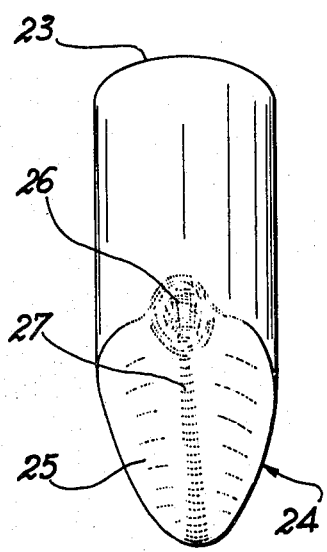
FIG. 8 shows a lens corresponding to the previous figure.

Referring to FIG. 8 which shows a lens 23, the lens face 24 located opposite to the cylindrical part is constituted by a toric surface 25 joined continuously and uniformly to a conical surface 26. This lens serves to scan a cylindrical part as described with reference to FIG. 7. There is no break in continuity at the point of junction 27 between the surfaces 25 and 26.

Figure 9:
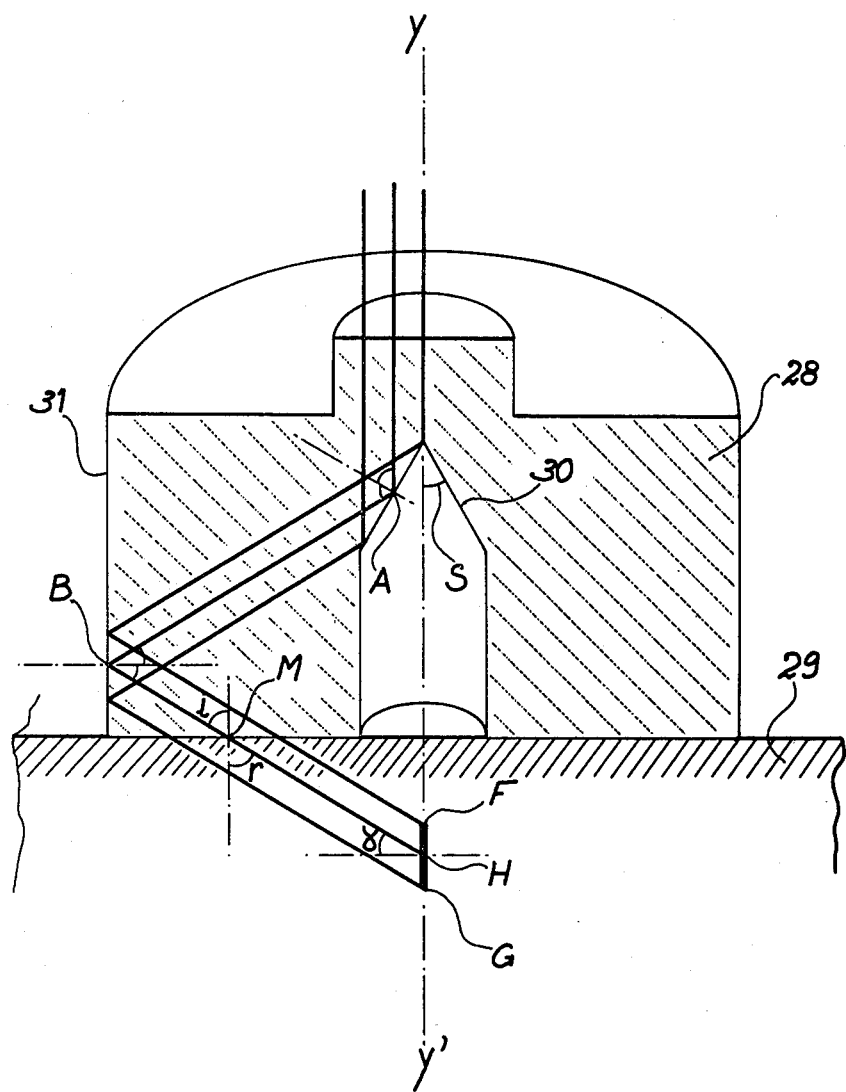
FIG. 9 shows an optical system according to the invention and constituted by an association of mirrors.

Referring now to FIG. 9, there is shown an optical system 28 in accordance with the invention for scanning a flat part 29 along a caustic FG which is normal to the surface of said part. This optical system is constituted by two mirrors which are coaxial with the caustic FG. One of these mirrors 30 has a conical shape whereas the other mirror 31 has a shape which depends on the part to be inspected. In the example of construction described, the mirror 31 has a cylindrical shape. The axis Y—Y' of the transducer which emits the ultrasonic beam for example in order to scan the part 29 is accordingly located in the line of extension of the caustic FG; the angle made between the end planes of incidence of the beam can in this case attain 360°. It is possible in particular to assign an angle of 180° to the emission and an angle of 180° to the reception.

Calculation of the mirrors described in the foregoing is based on the same principle as the calculation made in connection with FIG. 2. These two mirrors can advantageously be machined in the same block of aluminum, for example, in which case the scanning operation can take place by direct contact with the part 29.

If S designates the semivertical angle of the conical mirror 30, we may write:

$$S = i/2$$

and in the case of observation of a flat part of steel, for example, by means of an optical system formed of aluminum, the following parameters are defined:
$C_2 = 6300$ m/s (velocity of ultrasonic waves in aluminum);
$C_3 = 5900$ m/s (velocity of longitudinal waves in steel).

If the value $\gamma = 30°$ is chosen, the following angles are obtained:
$r = 60°$;
$i = 67.6°$;
$s = 33.8°$.

It will be noted that an ultrasonic beam has been employed in the different embodiments of the optical system according to the invention but it remains wholly apparent that this beam could have been of the electromagnetic type.

It will also have been noted that the different embodiments of the optical system according to the invention make it possible to scan either massive parts or parts having parallel faces such as blades, tubes, hollow spheres.

Finally, the different optical systems and lenses described in the foregoing can permit medical diagnosis when making use of an ultrasonic beam. In fact, lenses of this type which are traversed by an ultrasonic beam and have a caustic which is perpendicular to the surface of the body to be scanned make it possible to determine, for example, the differences in density in a part or organ of the human body in a plane which is perpendicular to the surface of said organ.

It is readily apparent that the different means adopted in the embodiments hereinabove described could have been replaced by equivalent means without thereby departing either from the scope or the spirit of the invention.

What is claimed is:

1. An optical system for scanning a part with a multiplicity of beams, wherein the constructional arrangement and position of the optical system with respect to the part are such that the caustic formed by said system within said part by refraction of the beam is concentrated on an axis at right angles to said part, by means of a lens opposite to said part which is contoured relative to the surface of the part, the angle of incidence of the refracted beams being constant with regard to said axis, the caustic being normal to the entry surface of the beam in the part, at the intersection between the caustic and the entry surface.

2. An optical system as defined in claim 1, wherein the caustic is formed after at least one reflection of the beam within the part as a result of refraction, said beam incident upon the optical system being parallel to the caustic within the part, said system being comprised of a lens, having a lens face receiving the incident beam and being flat and perpendicular to the caustic, said lens having another face opposite to the part, said another face being askew in relation to the caustic and being a portion of a surface of revolution having the same axis as the caustic.

3. An optical system as defined in claim 1, wherein the beam which is incident upon the optical system is parallel to the caustic within the part.

4. An optical system as defined in claim 1, wherein said system is constituted by a lens.

5. An optical system as defined in claim 1, wherein the lens face located opposite to the part has a conical shape in the case of a flat part.

6. An optical system as defined in claim 1, wherein the lens face located opposite to the part has a toric shape in the case of a spherical part.

7. An optical system as defined in claim 1, wherein in the case of a part having a cylindrical surface, the lens face located opposite to the part has a conical surface in the vicinity of the meridian plane of said part which contains the caustic, and a toric surface in the vicinity of the equatorial plane of said part which contains the caustic, these two surfaces being joined together in a continuous and uniform manner.

* * * * *

UNITED STATES PATENT AND TRADEMARK OFFICE
CERTIFICATE OF CORRECTION

PATENT NO. : 4,352,294
DATED     : October 5, 1982
INVENTOR(S) : Perdijon

It is certified that error appears in the above-identified patent and that said Letters Patent are hereby corrected as shown below:

On the title page:

Insert in the appropriate places in the heading of the patent the name of the inventor correctly spelled:

Under [19] : Perdijon

[75] Inventor : Jean Perdijon, Saint Ismier, France

*Signed and Sealed this*

*Twenty-fifth* Day of *January 1983*

[SEAL]

Attest:

GERALD J. MOSSINGHOFF

*Attesting Officer*   *Commissioner of Patents and Trademarks*